(12) United States Patent
Lewis et al.

(10) Patent No.: US 8,877,164 B2
(45) Date of Patent: *Nov. 4, 2014

(54) PHARMACEUTICAL AEROSOL FORMULATIONS FOR PRESSURIZED METERED DOSE INHALERS COMPRISING A SEQUESTERING AGENT

(75) Inventors: David Andrew Lewis, Wilts (GB); Brian John Meakin, Bath (GB); Maurizio Delcanale, Parma (IT); Fausto Pivetti, Sala Baganta (IT)

(73) Assignee: Chiesi Farmaceutici S.p.A., Parma (IT)

( * ) Notice: Subject to any disclaimer, the term of this patent is extended or adjusted under 35 U.S.C. 154(b) by 1027 days.

This patent is subject to a terminal disclaimer.

(21) Appl. No.: 11/361,562

(22) Filed: Feb. 24, 2006

(65) Prior Publication Data

US 2006/0193785 A1 Aug. 31, 2006

(30) Foreign Application Priority Data

Feb. 25, 2005 (EP) .................................... 05004233

(51) Int. Cl.
| | | |
|---|---|---|
| A61K 31/573 | (2006.01) | |
| A61K 47/04 | (2006.01) | |
| A61K 47/02 | (2006.01) | |
| A61K 9/12 | (2006.01) | |
| A61K 9/72 | (2006.01) | |
| A61K 31/58 | (2006.01) | |
| A61K 31/4704 | (2006.01) | |
| A61K 9/00 | (2006.01) | |

(52) U.S. Cl.
CPC ................ *A61K 9/008* (2013.01); *A61K 31/58* (2013.01); *A61K 31/573* (2013.01); *A61K 47/02* (2013.01); *A61K 31/4704* (2013.01)
USPC ........................................... 424/45; 514/181

(58) Field of Classification Search
CPC ..... A61K 9/0073; A61K 9/008; A61K 47/02; A61K 31/573
See application file for complete search history.

(56) References Cited

U.S. PATENT DOCUMENTS

| | | | | |
|---|---|---|---|---|
| 5,676,930 A | * | 10/1997 | Jager et al. ....................... | 424/45 |
| 6,716,414 B2 | * | 4/2004 | Lewis et al. ..................... | 424/45 |
| 7,381,402 B2 | * | 6/2008 | Lewis et al. ..................... | 424/45 |
| 2002/0025299 A1 | * | 2/2002 | Lewis et al. ..................... | 424/43 |
| 2003/0066525 A1 | * | 4/2003 | Lewis et al. .............. | 128/200.23 |
| 2003/0165435 A1 | | 9/2003 | Freund et al. | |
| 2004/0010003 A1 | | 1/2004 | Banholzer et al. | |
| 2004/0047809 A1 | * | 3/2004 | Lewis et al. ..................... | 424/45 |
| 2004/0058950 A1 | | 3/2004 | Meade et al. | |
| 2004/0235811 A1 | * | 11/2004 | Currie et al. ................... | 514/179 |

FOREIGN PATENT DOCUMENTS

| | | | |
|---|---|---|---|
| CA | 2495454 | | 9/2011 |
| EP | 1 157 689 A1 | | 11/2001 |
| EP | 1 466 594 | * | 10/2004 |
| EP | 1 466 594 A2 | | 10/2004 |
| EP | 1 595 531 A1 | | 11/2005 |
| WO | WO 94/13262 | | 6/1994 |
| WO | WO 95/17195 | | 6/1995 |
| WO | WO 96/40042 | | 12/1996 |
| WO | WO 00/30608 | | 6/2000 |
| WO | WO 00/78286 | * | 12/2000 |
| WO | WO 00/78286 A1 | | 12/2000 |
| WO | WO 01/07014 A1 | | 2/2001 |
| WO | WO 01/89480 | * | 11/2001 |
| WO | WO 01/89480 A1 | | 11/2001 |
| WO | WO 0187203 A1 | * | 11/2001 |
| WO | 03/074025 | | 9/2003 |
| WO | WO 03/074024 A1 | | 9/2003 |
| WO | WO 03/087097 A1 | | 10/2003 |
| WO | WO 2004/004704 A1 | | 1/2004 |
| WO | WO 2005/084640 A1 | | 9/2005 |

* cited by examiner

*Primary Examiner* — Daniel Sullivan
*Assistant Examiner* — Peter Anthopolos
(74) *Attorney, Agent, or Firm* — Brinks Gilson & Lione; Craig Buschmann

(57) ABSTRACT

Aerosol solution formulation for use in an aerosol inhaler which includes at least one active ingredient selected from 20-ketosteroids and quinolinone derivatives, a propellant containing a hydrofluoroalkane, a cosolvent, and a specific amount of a sequestering agent that stabilizes the formulation. By way of example, the stabilizing agent may be phosphoric acid or sulphuric acid.

15 Claims, No Drawings

PHARMACEUTICAL AEROSOL FORMULATIONS FOR PRESSURIZED METERED DOSE INHALERS COMPRISING A SEQUESTERING AGENT

CROSS-REFERENCE TO RELATED APPLICATIONS

The present application claims priority to European Application No. 05 004 233.2, filed Feb. 25, 2005, entitled "Pharmaceutical Aerosol Formulations for Pressurized Metered Dose Inhalers Comprising a Sequestering Agent," the entire contents of which are incorporated herein by reference.

BACKGROUND OF THE INVENTION

1. The Field of the Invention

The present invention relates to stable pharmaceutical solution formulations to be used with pressurized metered dose inhalers (MDIs) suitable for aerosol administration. In particular, the present invention relates to solutions to be used with pressurized metered dose inhalers (MDIs), which are suitable for aerosol administration containing an active ingredient highly susceptible to chemical degradation selected from a group consisting of 20-ketosteroids and quinolinone derivatives, which is stabilized by the presence of a sequestering agent.

2. The Relevant Technology

Pressurized metered dose inhalers are well known devices for administering pharmaceutical products to the respiratory tract by inhalation.

Drugs commonly delivered by inhalation include bronchodilators such as $\beta_2$-agonists and anticholinergics, corticosteroids, anti-leukotrienes, anti-allergics and other materials that may be efficiently administered by inhalation, thus increasing the therapeutic efficacy and reducing side effects.

MDIs use a propellant to expel droplets containing the pharmaceutical product to the respiratory tract as an aerosol.

Since the halogenated propellants such as chlorofluorocarbons, commonly called Freons or CFCs, have been banned as known to deplete the ozone layer, HFAs and in particular 1,1,1,2-tetrafluoroethane (HFA 134a) and 1,1,1,2,3,3,3-heptafluoropropane (HFA 227) have been acknowledged to be the best candidates for non-CFC propellants and a number of medicinal aerosol formulations using such HFA propellant systems have been disclosed.

Formulations for aerosol administration via MDIs can be solutions or suspensions. Solution formulations offer the advantage of being homogeneous with the active ingredient and excipients completely dissolved in the propellant vehicle or its mixture with suitable co-solvents such as ethanol. Solution formulations also obviate physical stability problems associated with suspension formulations so assuring more consistent uniform dosage administration.

Recently many types of active ingredients have been reformulated as solutions in non CFC hydrofluorocarbon (HFC) propellants with ethanol.

However, it has been noticed in this kind of formulations that due to the higher polarity of the HFA propellants, in particular of HFA 134a having a dielectric constant of D≥9.5, with respect to CFC vehicles of D≤2.3, the active ingredient may suffer of chemical stability problems and degrade during storage. Chemical degradation is especially problematic when the compound is dissolved in the formulation.

Chemical degradation of the active ingredient may occur by various mechanisms, the most significant being the oxidative degradation by molecular oxygen, catalysed by the presence of heavy metal ions, such as aluminium, ferric or cupric ions, and the hydrolysis or esterification phenomena which are pH dependent.

Consequently, attempts to increase the stability of the active ingredients have been directed to lower the pH and minimize the amount of heavy metal ions in the aerosol formulation.

As to the pH lowering, WO 94/13262 suggests using acids as stabilizers for reducing the interaction of the ative ingredient with the cosolvent and/or water present in the solution formulation. Most examples related to ipratropium bromide, an anticholinergic drug and an example was presented for a $\beta_2$-agonist, i.e., fenoterol. No difference is made in the application between the use of organic and inorganic acids and organic acids are preferably used. In WO 01/89480 of the applicant, stability data of a HFA 134a solution formulation containing 32 adrenergic agonists and in particular formoterol and 8-hydroxy-5-[(1R)-1-hydroxy-2-[[(1R)-2-(4-methoxyphenyl)-1-methylethyl]amino]ethyl]-2(1H)-quinolinone hydrochloride (TA 2005) stabilized by different amounts of HCl 1.0M or 0.08M were reported. Phosphoric acid is mentioned but not exemplified.

In WO 2003/087097 propellant-free inhalable solutions or suspensions containing a combination of $\beta_2$-agonists and anticholinergics have been described. Both organic and inorganic acids were used to adjust the pH. Examples of particularly suitable inorganic acids include hydrochloric acid, hydrobromic acid, nitric acid, sulphuric acid and/or phosphoric acid. According to this document, it is particularly preferred to use hydrochloric acid to adjust the pH. Analogous formulations have been described in WO 2004/004704 referred to propellant-free inhalable solutions or suspensions containing a combination of anticholinergics and PDE-IV inhibitors.

As to the minimization of heavy metal ions, WO 00/78286 ('286) and WO 00/30608 ('608), propose the use of aerosol containers with inert interior surfaces.

WO 96/40042 disclosed that aqueous formulations of triamcinolone acetonide in neutral or basic solutions undergo oxidative degradation catalyzed by trace levels of metal ions, especially copper, and proposes the use of EDTA as sequestering agent and/or adjusting pH. The rate of disappearance of triamcinolone acetonide in aqueous solution exhibited a dependency on the buffer concentration at constant pH and ionic strength. EDTA even in a very low concentration had a profound inhibitory effect of the degradation.

Solution formulations of flunisolide in HFC/HFA propellants were disclosed in WO 95/17195, where it is indicated that chemical stability may be enhanced by using additives like water, sorbitan trioleate, and cetylpyridinium chloride, and also that certain containers such as glass and resin coated aluminum enhance chemical stability and/or minimize the absorption of flunisolide onto the container wall.

BRIEF SUMMARY OF THE INVENTION

The present invention improves the chemical stability of active ingredients subjected to oxidative degradation and selected from a group consisting of 20-ketosteroids and quinolinone derivatives in an aerosol formulation comprising a liquefied HFA propellant and a co-solvent selected from pharmaceutically acceptable alcohols. This is achieved by adding a chelating or sequestering agent selected from a group consisting of phosphoric acid and sulphuric acid. The sequestering agent stabilizes the metal ions, present in traces in the solution, in a less active state thereby making them less available as catalysts for oxidative reactions in such an aprotic HFA propellant/cosolvent system as that of the formulations of the invention. Preferably the inorganic acid is highly concentrated.

Since the aerosol formulations of the invention may include more than one active ingredient that may be subjected to the two different mechanisms of degradation, the oxidation reaction and the hydrolysis or esterification, it does appear convenient to employ an additive to the formulation which acts both as a pH adjuster and a sequestering or chelating agent.

According to the invention it has been found that an inorganic acid, acting through the two different mechanisms of action, can be safely utilized in a HFA propellant/cosolvent system and in particular in a HFA propellant/ethanol system to prepare formulations stable, preferably at room temperature, for a pharmaceutically acceptable shelf-life.

Accordingly, the present invention provides an aerosol formulation, which comprises at least one active ingredient selected from a group consisting of 20-ketosteroids and quinolinone derivatives, a liquefied HFA propellant, a co-solvent selected from pharmaceutically acceptable alcohols, and a sequestering agent selected from a group consisting of phosphoric acid and sulphuric acid, wherein the chemical stability of the active ingredients is improved. Preferably the inorganic acid is highly concentrated.

Preferably the 20-ketosteroids are selected from budesonide, flunisolide, triamcinolone acetonide, dexamethasone, and betamethasone 17 valerate.

Alternatively, specific amounts of phosphoric acid in a specific concentration can be used as pH adjuster in aerosol solution formulations comprising 8-hydroxy-5-[(1R)-1-hydroxy-2-[[(1R)-2-(4-methoxyphenyl)-1-methylethyl]amino] ethyl]-2(1H)-quinolinone and its These and other objects and features of the present invention will become more fully apparent from the following description and appended claims, or may be learned by the practice of the invention as set forth hereinafter.

DETAILED DESCRIPTION OF THE PREFERRED EMBODIMENTS

According to the present invention, there is provided a pharmaceutical composition comprising at least one active ingredient in a solution of a liquefied HFA propellant, a co-solvent selected from pharmaceutically acceptable alcohols and a specific amount of an additive acting as sequestering agent.

The formulation is preferably a solution in which the active ingredient is completely dissolved. However in case of combinations, one of the two active ingredients could be present in suspension. The co-solvent is usually an alcohol, preferably ethanol.

The active ingredient may be any compound which is suitable for aerosol administration from an MDI, is soluble in the HFA propellant/cosolvent system, and characteristically exhibits significant degradation or decomposition in the HFA propellant/cosolvent system.

The active ingredient is or comprises at least one compound which contains a group or residue or radical or side chain susceptible to chemical degradation and in particular to oxidative degradation. Said group or residue or radical or side chain may be constituted by or contain an epoxydic, acidic, aldehydic, alcoholic, amminoalcoholic group or a double bond, in particular a conjugated double bond. The active ingredient may further comprise active ingredients which undergo a decomposition and /or degradation that can be attributed to hydrolysis and esterification, reactions which are typically pH dependent.

A first class of compounds representative of the invention is that of steroids, in particular glucocorticosteroids and expecially certain 20-ketosteroids.

In fact, it has been reported that steroids in particular having a C-20 ketone and an OH group at the C-17 position or the C-21 position or both are subject to enhanced chemical degradation when stored in contact with a metal container, in particular the metal oxide e.g., A1203 layer that forms on the interior surface of the container.

A typical core structure for a large number of natural and synthetic 20-ketosteroids has been shown in WO 0078286:

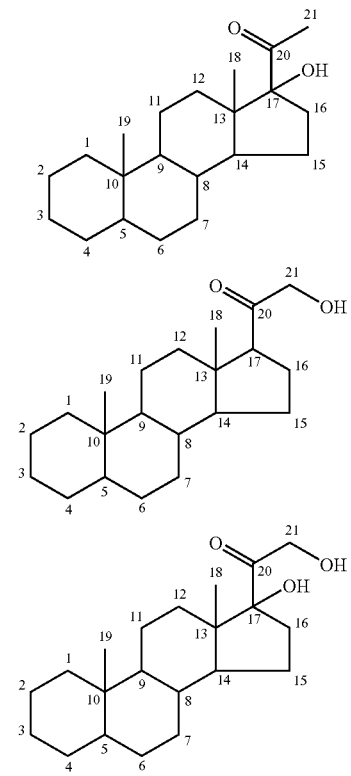

Particularly preferred 20-keto steroids are budesonide, flunisolide, triamcinolone acetonide, dexamethasone, and betamethasone 17-valerate, all of which have an OH group at the C-21 position. Other kinds of steroids such as ciclesonide may benefit from the formulation of the present invention.

A second class of compounds representative of the invention is the chemical class of phenylalkylamino $\beta_2$-adrenergic agonists selected from quinolinone derivatives belonging to the formula:

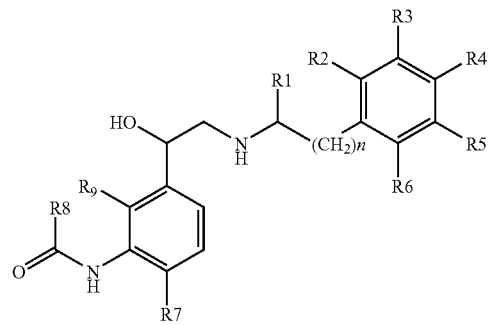

wherein $R_1$ is methyl and $R_2$ is hydrogen or $R_1$ and $R_2$ form a methylenic bridge —$(CH_2)_n$— with n is 1 or 2, R$_3$, R$_4$, R$_5$ and R$_6$ are each independently hydrogen, hydroxy, a straight chain or branched C$_1$-C$_4$ alkyl, a straight chain or branched C$_1$-C$_4$ alkyl substituted with one or more halogen atoms and/or hydroxy groups, halogen, straight chain or branched C$_1$-C$_4$ alkoxy, R$_7$ is hydrogen, hydroxy, straight chain or branched C$_1$-C$_4$ alkyl, straight chain or branched C$_1$-C$_4$ alkoxy and R$_8$ and R$_9$ are independently hydrogen, C$_1$-C$_4$ alkyl or form together a vinylene (—CH=CH—) or an ethylene (—CH$_2$CH$_2$—) radical, and enantiomers, salts and solvates thereof.

Particularly preferred are the compounds wherein:

R$_1$ is methyl, R$_4$ is methoxy, R$_2$, R$_3$, R$_5$, R$_6$, R$_8$, R$_9$ are hydrogen, R$_7$ is hydroxy and n=1 (formoterol), and R$_1$ is methyl, R$_4$ is methoxy, R$_2$, R$_3$, R$_5$, R$_6$ are hydrogen, R$_7$ is hydroxy, R$_8$ and R$_9$ together form a vinylene (—CH=CH—) radical and n=1, that is the 8-hydroxy-5-[(1R)-1-hydroxy-2-[[(1R)-2-(4-methoxyphenyl)-1-methylethyl]amino]ethyl]-2-(1H)-quinolinone whose hydrochloride salt has been also reported with the experimental codes of TA 2005 and CHF 4226.

Active ingredients from the above mentioned class of compounds may be used alone, in combination with each other and/or combined with further classes of compounds for example antimuscarinic quaternary ammonium compounds such as ipratropium bromide, oxitropium bromide, tiotropium bromide and analogous.

Because the aerosol formulations of the invention may comprise more than one active ingredient that can be subjected to the two different mechanisms of degradation, the oxidation reaction and the hydrolysis or esterification, the presence in the formulation of an additive acting both as a pH adjuster and as sequestering or chelating agent, to stabilize the active ingredients, is particularly preferred. Said additive is an inorganic acid selected from phosphoric and sulphuric acid.

Both these acids fulfil the combined action of sequestering the metal ions so inhibiting the catalysis of oxidation reactions and adjusting the apparent pH in the desired interval.

For the purposes of the present invention phosphoric acid also referred to as orthophosphoric acid, metaphosphoric acid and white phosphoric acid is the preferred one.

While phosphoric and sulphuric acid have been mentioned before, as possible inorganic acids employable, in connection with HFA propellant based aerosol formulations, to adjust the pH, none of the examples of the prior art disclose their use in a HFA propellant/cosolvent system as sequestering agent for the stabilization of 20-ketosteroids and quinolinone derivatives.

Embodiments of the invention include the use of specific amounts of phosphoric acid in a specific concentration, as pH adjuster, in aerosol solution formulations comprising 8-hydroxy-5-[(1R)-1-hydroxy-2-[[(1R)-2-(4-methoxyphenyl)-1-methylethyl]amino]ethyl]-2(1H)-quinolinone and its hydrochloride salt. Further details can be found in International Publication No. WO 2005/084640, EP Application No. 04011424.1 and U.S. patent application Ser. No. 11/065,569, which claims the benefit U.S. Provisional Application No. 60/547,798, each of the foregoing being incorporated herein by reference.

The phosphoric acid has a concentration preferably equal or higher than about 10 M, preferably higher than about 12 M and in particular about 15 M. In the example that follows 85% i.e. 15.2M phosphoric acid has been used.

In particular, it is preferred to add phosphoric acid in an amount equivalent to 0.0004 to 0.040% w/w of 15M phosphoric acid, based on the total weight of the composition, preferably 0.0008 to 0.020% w/w of 15M phosphoric acid, based on the total weight of the composition, more preferably 0.001 to 0.010% w/w of 15M phosphoric acid, based on the total weight of the composition, still more preferably 0.002 to 0.0075% w/w of 15 M phosphoric acid, based on the total weight of the composition.

As far as sulphuric acid is concerned, preferably 0.075 M sulphuric acid is used. In particular, it is preferred to add sulphuric acid in an amount equivalent to 0.0005 to 0.02% w/w of 0.075 M sulphuric acid, based on the total weight of the composition, preferably 0.001 to 0.01% w/w of 0.075 M sulphuric acid, based on the total weight of the composition, more preferably 0.001 to 0.0072% w/w of 0.075 M sulphuric acid, based on the total weight of the composition, even more preferably 0.002 to 0.0054% w/w of 0.075 M sulphuric acid, based on the total weight of the composition.

A still high concentrated phosphoric acid other than 15 M or sulphuric acid other than 0.075 M can be utilized. In this case, the person skilled in the art will be able to determine the right percent amount in view of the disclosure in the present application.

The pH of the formulation, more appropriately defined as "apparent" pH, is preferably comprised between 2.5 and 5.5.

The attribution 'apparent' is used as pH is indeed characteristic of aqueous liquids where water is the dominant component (Mole Fraction>0.95). In relatively aprotic solvents, such as the HFA-ethanol vehicles used in these studies, protons are non-hydrated; their activity coefficients differ significantly from those in aqueous solution. Although the Nernst equation with respect to EMF applies and the pH-meter glass electrode system will generate a variable millivolt output according to proton concentration and vehicle polarity, the "pH" meter reading is not a true pH value. The meter reading represents an apparent pH or acidity function (pH').

The effect of the acid on the acidity function (pH' or apparent pH) of the solution of the active compound can be determined in a model vehicle system commercially available (HFA 43-10MEE, Vertrel XF, Dupont), according to a method developed by the applicant and described in EP 1157689.

The amount of acid to be added to reach the desired apparent pH will be predetermined in the model vehicle reported before.

The formulations of the present invention will be preferably contained in cans having part or all of the internal surfaces made of stainless steel, anodized aluminium or lined with an inert organic coating. Examples of preferred coatings are epoxy-phenol resins, perfluoroalkoxyalkane, perfluoroalkoxyalkylene, perfluoroalkylenes such as polytetrafluoroethylene, fluorinated-ethylene-propylene, polyether sulfone and mixtures of fluorinated-ethylene-propylene and polyether sulfone. Other suitable coatings could be polyamide, polyimide, polyamideimide, polyphenylene sulfide or their combinations.

The most preferred coatings are perfluoroalkoxyalkane, perfluoroalkoxy-alkylene, perfluoroalkylenes such as polytetrafluoroethylene and fluorinated-ethylene-propylene and copolymers of fluorinated-ethylene-propylene polyether sulfones. Fluorocarbon polymers are marketed under trademarks such as Teflon®.

To further improve the stability, cans having a rolled-in rim and preferably a part or full rollover rim can be used.

The formulation is actuated by a metering valve capable of delivering a volume of between 50 μl and 100 μl.

The hydrofluorocarbon propellant is preferably selected from the group of HFA 134a, HFA 227 and mixtures thereof.

The pharmaceutical formulations of the invention may further contain excipients and in particular a low volatility component in order to increase the mass median aerodynamic diameter (MMAD) of the aerosol particles on actuation of the inhaler.

However, in a preferred embodiment the addition of other components to the formulation is avoided.

According to a further aspect of the present invention there is provided a method of filling an aerosol inhaler with a composition of the invention, the method comprising:

(a) adding one or more active ingredients to one or more co-solvents optionally containing a further active ingredient or excipient or an appropriate amount of a low volatility component;

(b) filling the device with said solution;

(c) adding a pre-determined amount of a phosphoric or sulphuric acid;

(d) adding a propellant containing a hydrofluoroalkane (HFA); and (e) crimping with valves and gassing.

Other features of the invention will become apparent in the course of the following descriptions of exemplary embodiments which are given for illustration of the invention and are not intended to be limiting thereof.

The stabilizing effects of phosphoric acid have been tested in a solution formulation of a 20-ketosteroid, budesonide. The results show that small amounts of 85% (15.2 M) phosphoric acid (0.00074 to 0.0015% w/w) reduce the formation of the main oxidative degradation product, the 21-aldehyde. Further, amounts ranging from 0.0031 to 0.0063% w/w of 15.2 M phosphoric acid stabilize a formulation which combines budesonide and TA2005 as active ingredients.

It has been also demonstrated that the chemical stability of TA 2005, a quinolinone derivative is improved by 0.075 M sulphuric acid, present in a concentration of 0.0018 to 0.0054% w/w.

In the following examples and throughout this specification, all parts and percentages are by weight, and all temperatures are in degrees Celsius, unless expressly stated to be otherwise.

The active ingredient/s in the pressurized metered dose inhaler according to the present invention has a percent recovery equal or higher than 95% after 6 months, preferably after 12 months at 25° C. and 60% relative humidity.

EXAMPLE 1

A formulation for delivering a nominal dose of 200 μg of budesonide per actuation was prepared and filled in anodized aluminium canisters fitted with a metering valve having a 50 μl metering chamber.

A stability study was carried out by storing the formulation in upright (Up) and inverted (Inv) cans at 40° C. and 75% relative humidity. After three months of storage under these conditions the percent recovery of the active ingredient was very good. At the same time, the addition of small quantities of phosphoric acid appears to reduce the main oxidation degradation product, which is the 21-aldehyde content of the budesonide formulation.

| Budesonide 200 μg/50 μl, 15% EtOH, 0.15% $H_2O$ w/w | | | | | | | | | | | | |
|---|---|---|---|---|---|---|---|---|---|---|---|---|
| Phosphoric Acid (15.2 M) | | Up/ | | Recovery t = 3 days | | | Recovery t = 1 month | | | | Recovery t = 3 month | |
| | | | Bud | 21-Aldehyde | | Budes-onide | | 21-Aldehyde | | Budes-onide | | |
| mg | % w/w | Inv | mg | μg | % | mg | % | μg | % | mg | % | |
| 0.2 | 0.0015 | Up | 50 | 37 | 0.08 | 50 | 99 | 72 | 0.15 | 49 | 98 | |
| | | | 50 | 39 | | 50 | | 73 | | 49 | | |
| | | Inv | | | | 50 | 99 | 171 | 0.35 | 49 | 98 | |
| | | | | | | 49 | | 171 | | 49 | | |
| 0.1 | 0.00074 | Up | 51 | 43 | 0.08 | 50 | 98 | 85 | 0.21 | 49 | 98 | |
| | | | 50 | 39 | | 49 | | 118 | | 49 | | |
| | | Inv | | | | 48 | 97 | 188 | 0.39 | 49 | 97 | |
| | | | | | | 49 | | 190 | | 49 | | |
| 0 | | Up | 51 | 39 | 0.08 | 50 | 98 | 174 | 0.35 | 49 | 97 | |
| | | | 51 | 40 | | 50 | | 174 | | 49 | | |
| | | Inv | | | | 50 | 98 | 286 | 0.55 | 48 | 95 | |
| | | | | | | 50 | | 256 | | 48 | | |

EXAMPLE 2

A formulation of 8-hydroxy-5-[(1R)-1-hydroxy-2-[[(1R)-2-(4-methoxyphenyl)-1-methyl ethyl]amino]ethyl]-2(1H)-quinolinone hydrochloride (TA 2005) for delivering a nominal dose of 1 μg of active ingredient per actuation, was prepared with the following formulation:

| | Amounts | | |
|---|---|---|---|
| | Per unit | | Nominal dose |
| Components | mg | % | μg |
| TA 2005 | 0.15 | 0.0016 w/v | 1 |
| Ethanol | 1650 | 15 w/w | — |
| $H_2SO_4$ 0.075 M | 0.2-0.6 | 0.18-0.54 w/w | — |
| HFA 134a q.s. to 9.72 ml | | — | — |

The formulation (120 actuations/canister, overage of 30 actuations) was filled in aluminium canisters having the internal surface coated with Teflon and fitted with a metering valve having a 63 μl metering chamber.

A stability study was carried out by storing the formulation in upright cans at 40° C. The percent recovery of the active ingredient after one month of storage under these conditions is reported in the following:

TA 2005 stability in presence of sulphuric acid -
Recovery after 1 month storage in upright cans at 40° C.

| Sulphuric Acid (0.075 M) | | Recovery t = 0 | Recovery t = 1 month | |
|---|---|---|---|---|
| mg | % w/w | mcg | mcg | % |
| 0.2 | 0.0018 | 153 | 151 | 98 |
| 0.4 | 0.0036 | 153 | 153 | 100 |
| 0.6 | 0.0054 | 155 | 153 | 98 |

The results show that the inorganic acids of the invention are efficacious to improve the chemical stability of the 20-ketosteroid budesonide and the quinolinone derivative TA 2005.

EXAMPLE 3

Three batches of HFA propellant/ethanol solutions were formulated combining approximately 0.30 mg TA2005 and approximately 30 mg Budesonide ("Bud") varying the phosphoric acid (15M) and water quantities. The formulations were packaged in Teflon-coated aluminum canisters fitted with a halobutyl or butyl rubber (butyl) valve.

The canisters were stored in inverted position at 25° C. and 60% relative humidity up to 12 months. A stability study was carried out at different points in time. More detailed results are reported in the table below.

| Batch | % H20 | % w/w H3PO4 | % TA2005 3 months | % Bud 3 months | % TA2005 6 months | % Bud 6 months | % TA2005 12 months | % Bud 12 months |
|---|---|---|---|---|---|---|---|---|
| 1 | 0 | 0.0031 | 99.3 | 100.0 | 98.0 | 98.7 | 95.7 | 98.7 |
| 2 | 0.3 | 0.0031 | 98.8 | 99.0 | 98.2 | 98.7 | 95.6 | 98.6 |
| 3 | 0.3 | 0.0063 | 98.7 | 99.3 | 97.9 | 99.2 | 95.6 | 98.7 |

The total percentage of TA2005 degradation products resulted between 1.2 and 2%. The total percentage of Budesonide degradation products resulted between 0.64 and 1.7%.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An aerosol formulation consisting of:
   a 20-ketosteroid;
   a liquefied HFA propellant, a co-solvent selected from pharmaceutically acceptable alcohols; and
   an agent selected from the group consisting of phosphoric acid present in an amount equivalent to 0.0004 to 0.040% w/w of 15 M phosphoric acid, based on the total weight of the formulation and sulphuric acid present in an amount equivalent to 0.0005 to 0.02% w/w of 0.075 M sulphuric acid, based on the total weight of the composition that sequesters a metal ion present in the formulation, thereby improving the chemical stability of the active ingredient;
   wherein said co-solvent is ethanol; and,
   wherein said formulation is in the form of a solution in which said 20-ketosteroid is completely dissolved.

2. The formulation according to claim 1 wherein said liquefied HFA propellant is at least one member selected from the group consisting of HFA 134a, HFA 227, and mixtures thereof.

3. The formulation according to claim 1 wherein said phosphoric acid is present in an amount equivalent to 0.0008 to 0.020% w/w of 15M phosphoric acid, based on the total weight of the formulation.

4. The formulation according to claim 1 wherein said sulphuric acid is present in an amount equivalent to 0.001 to 0.01% w/w of 0.075 M sulphuric acid, based on the total weight of the formulation.

5. The formulation according to claim 1 wherein said co-solvent is present in an amount of 6% to 30% w/w.

6. The formulation according to claim 1 wherein said co-solvent is present in an amount of 6% to 25% w/w.

7. The formulation according to claim 1 wherein said 20-ketosteroid is selected from budesonide, flunisolide, triamcinolone acetonide, dexamethasone, and betamethasone 17 valerate.

8. The formulation according to claim 7 wherein said 20-ketosteroid is budesonide.

9. A pressurized metered dose inhaler comprising:
   a can configured to store a formulation for use in an inhaler; and
   the formulation in said can, the formulation being suitable for aerosol administration, the formulation consisting of:
   a 20-ketosteroid;
   a liquefied HFA propellant, a co-solvent selected from pharmaceutically acceptable alcohols; and
   an agent selected from the group consisting of: phosphoric acid present in an amount equivalent to 0.0004 to 0.040% w/w of 15 M phosphoric acid, based on the total weight of the formulation and sulphuric acid present in an amount equivalent to 0.0005 to 0.02% w/w of 0.075 M sulphuric acid, based on the total weight of the composition that sequesters a metal ion in the formulation, thereby improving the chemical stability of the active ingredient; and
   wherein said co-solvent is ethanol; and,
   wherein said formulation is in the form of a solution in which said 20-ketosteroid is completely dissolved.

10. The pressurized metered dose inhaler according to claim 9, wherein the can comprises internal metallic surfaces and part or all of the internal metallic surfaces are stainless steel, anodized aluminium or lined with an inert organic coating.

11. The pressurized metered dose inhaler according to claim 10, which is lined with an inert organic coating selected from the group consisting of epoxy-phenol resins, perfluoroalkoxyalkanes, perfluoroalkoxyalkylenes, perfluoroalkylenes, polyether sulfones, mixtures of fluorinated-ethylene-propylene and polyether sulfone, and mixtures thereof.

12. The formulation of claim 1, wherein the agent is phosphoric acid.

13. The formulation of claim 1, wherein the agent is sulphuric acid.

14. The formulation of claim 8, wherein the agent is phosphoric acid.

15. The formulation of claim 8, wherein the agent is sulphuric acid.

* * * * *

UNITED STATES PATENT AND TRADEMARK OFFICE
CERTIFICATE OF CORRECTION

PATENT NO. : 8,877,164 B2  
APPLICATION NO. : 11/361562  
DATED : November 4, 2014  
INVENTOR(S) : David Andrew Lewis et al.

Page 1 of 1

It is certified that error appears in the above-identified patent and that said Letters Patent is hereby corrected as shown below:

On the Title Page

Left column, item (75), after "Pivetti," replace "Sala Baganta" with --Sala Baganza--.

Signed and Sealed this  
Fifth Day of May, 2015

Michelle K. Lee  
*Director of the United States Patent and Trademark Office*